United States Patent
Dwyer

(10) Patent No.: US 12,350,433 B2
(45) Date of Patent: *Jul. 8, 2025

(54) MOISTURE REMOVAL AND CONDENSATION AND HUMIDITY MANAGEMENT APPARATUS FOR A BREATHING CIRCUIT

(71) Applicant: Medline Industries, LP, Springfield, IL (US)

(72) Inventor: Daniel Patrick Dwyer, Cary, NC (US)

(73) Assignee: Medline Industries, LP, Springfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/534,417

(22) Filed: Dec. 8, 2023

(65) Prior Publication Data
US 2024/0139457 A1 May 2, 2024

Related U.S. Application Data

(63) Continuation of application No. 17/020,065, filed on Sep. 14, 2020, now Pat. No. 11,865,264, which is a
(Continued)

(51) Int. Cl.
*A61M 16/08* (2006.01)
*A61M 16/16* (2006.01)

(52) U.S. Cl.
CPC .... *A61M 16/0808* (2013.01); *A61M 16/0816* (2013.01); *A61M 16/0875* (2013.01);
(Continued)

(58) Field of Classification Search
CPC .............. A61M 16/01; A61M 16/0087; A61M 16/009–0093; A61M 16/0486;
(Continued)

(56) References Cited

U.S. PATENT DOCUMENTS 2,362,985 A  11/1944 Brown, Jr.
2,702,089 A   2/1955 Engelder
(Continued)

FOREIGN PATENT DOCUMENTS

EP    0533644 A2   3/1993
EP    2283888 A1   2/2011
(Continued)

OTHER PUBLICATIONS

Raesystems By Honeywell, Technical Note TN-157: Moisture Exchange Tubes for Humidity Control of Test Gases, Jul. 29, 2014, 2 pages.

*Primary Examiner* — Colin W Stuart
*Assistant Examiner* — Douglas Y Sul
(74) *Attorney, Agent, or Firm* — Quarles & Brady LLP

(57) ABSTRACT

A moisture removal apparatus for a breathing circuit may include a breathing gas conduit configured to receive a flow of breathing gas having a first humidity level. The apparatus may include a dry gas conduit adjacent to at least a portion of the breathing gas conduit, the dry gas conduit configured to receive a flow of dry gas having a second humidity level lower than the first humidity level. The apparatus may also include a feeding conduit extending through at least a portion of the dry gas conduit, the feeding conduit configured to introduce the dry gas into the dry gas conduit. The apparatus may further include a moisture transmission pathway configured to enable transfer of moisture from the breathing gas to the dry gas based on the humidity differential.

20 Claims, 2 Drawing Sheets

Related U.S. Application Data continuation of application No. 15/788,733, filed on Oct. 19, 2017, now Pat. No. 10,773,043.

(60) Provisional application No. 62/410,195, filed on Oct. 19, 2016.

(52) U.S. Cl.
CPC ......... *A61M 16/16* (2013.01); *A61M 2205/75* (2013.01); *A61M 2205/7536* (2013.01)

(58) Field of Classification Search
CPC .............. A61M 16/08; A61M 16/0808; A61M 16/0875; A61M 16/0816; A61M 16/10; A61M 16/1065; A61M 16/22; A61M 2205/7536; A61M 2205/3606; A61M 2039/226; A61M 2039/229; B01D 2313/00; B01D 2319/00; B01D 53/22; B01D 53/268; B01D 63/00; B01D 2257/80; B01D 63/08; B01D 63/085

See application file for complete search history.

(56) References Cited

U.S. PATENT DOCUMENTS

| | | | |
|---|---|---|---|
| 3,735,558 A | 5/1973 | Skarstrom et al. | |
| 3,747,598 A | 7/1973 | Cowans | |
| 4,146,597 A | 3/1979 | Eckstein et al. | |
| 4,155,961 A | 5/1979 | Benthin | |
| 4,200,094 A | 4/1980 | Gedeon et al. | |
| 4,220,535 A * | 9/1980 | Leonard ................ | B01D 53/22 210/321.89 |
| 4,232,667 A | 11/1980 | Chalon et al. | |
| 4,318,398 A | 3/1982 | Oetjen et al. | |
| 4,355,636 A | 10/1982 | Oetjen et al. | |
| 4,381,267 A | 4/1983 | Jackson | |
| 4,637,384 A | 1/1987 | Schroeder | |
| 4,808,201 A | 2/1989 | Kertzman | |
| 4,897,359 A | 1/1990 | Oakley et al. | |
| 5,042,500 A | 8/1991 | Norlien et al. | |
| 5,062,145 A | 10/1991 | Zwaan et al. | |
| 5,097,898 A | 3/1992 | Verkaart | |
| 5,501,212 A | 3/1996 | Psaros | |
| 6,014,971 A | 1/2000 | Danisch et al. | |
| 6,213,120 B1 | 4/2001 | Block et al. | |
| 6,220,245 B1 | 4/2001 | Takabayashi et al. | |
| 6,516,536 B2 | 2/2003 | Ryden | |
| 6,523,538 B1 * | 2/2003 | Wikefeldt ......... | A61M 16/1075 128/205.12 |
| 6,662,802 B2 | 12/2003 | Smith et al. | |
| 6,769,431 B2 | 8/2004 | Smith et al. | |
| 6,776,820 B2 | 8/2004 | Bikson et al. | |
| 6,953,354 B2 | 10/2005 | Edirisuriya et al. | |
| 7,097,690 B2 | 8/2006 | Usher et al. | |
| 7,476,212 B2 * | 1/2009 | Spearman ........... | A61M 13/003 604/23 |
| 7,588,029 B2 | 9/2009 | Smith et al. | |
| 7,802,569 B2 | 9/2010 | Yeates et al. | |
| 8,037,882 B2 | 10/2011 | Smith et al. | |
| 8,105,410 B2 | 1/2012 | Roth et al. | |
| 8,230,857 B2 * | 7/2012 | Cewers ............... | A61M 16/205 128/204.22 |
| 8,236,081 B2 | 8/2012 | Roth et al. | |
| 8,453,641 B2 | 6/2013 | Payton et al. | |
| 8,616,202 B2 | 12/2013 | Tatkov et al. | |
| 8,893,748 B2 | 11/2014 | Malas et al. | |
| 9,067,036 B2 | 6/2015 | Korneff et al. | |
| 9,827,393 B2 | 11/2017 | Smith et al. | |
| 10,773,043 B2 * | 9/2020 | Dwyer ............. | A61M 16/0816 |
| 11,865,264 B2 * | 1/2024 | Dwyer ............. | A61M 16/0875 |
| 2003/0230306 A1 | 12/2003 | Castor et al. | |
| 2006/0021615 A1 | 2/2006 | Kertzman | |
| 2006/0162554 A1 | 7/2006 | Kelley | |
| 2007/0157929 A1 | 7/2007 | Radomski et al. | |
| 2007/0157931 A1 | 7/2007 | Parker et al. | |
| 2008/0110458 A1 | 5/2008 | Srinivasan et al. | |
| 2008/0229605 A1 | 9/2008 | Brown | |
| 2009/0088656 A1 | 4/2009 | Levitsky et al. | |
| 2011/0315140 A1 | 12/2011 | Shuman | |
| 2013/0098360 A1 | 4/2013 | Hurmez et al. | |
| 2013/0112201 A1 | 5/2013 | Graham et al. | |
| 2013/0303977 A1 | 11/2013 | Spearman et al. | |
| 2014/0261416 A1 * | 9/2014 | Arcilla ............. | A61M 16/0891 128/203.14 |
| 2014/0283829 A1 | 9/2014 | Miller | |
| 2015/0048530 A1 | 2/2015 | Cheung et al. | |
| 2015/0083121 A1 | 3/2015 | Fisher et al. | |
| 2015/0101607 A1 | 4/2015 | Virr et al. | |
| 2015/0209528 A1 | 7/2015 | Lee et al. | |
| 2016/0045702 A1 | 2/2016 | Milne et al. | |
| 2016/0287832 A1 * | 10/2016 | Cortez, Jr. ........ | A61M 16/0003 |
| 2016/0303342 A1 | 10/2016 | Dwyer et al. | |
| 2018/0104433 A1 | 4/2018 | Dwyer et al. | |
| 2020/0206681 A1 * | 7/2020 | Hartnett ............... | B01D 53/227 |

FOREIGN PATENT DOCUMENTS

| | | |
|---|---|---|
| EP | 2335760 A1 | 6/2011 |
| GB | 1431558 A | 4/1976 |
| GB | 2139110 A | 11/1984 |
| JP | 2000024111 A | 1/2000 |
| WO | 9616689 A1 | 6/1996 |

\* cited by examiner

MOISTURE REMOVAL AND CONDENSATION AND HUMIDITY MANAGEMENT APPARATUS FOR A BREATHING CIRCUIT

CROSS REFERENCE

The present application is a continuation of U.S. patent application Ser. No. 17/020,065, filed Sep. 14, 2020, which is a continuation of U.S. patent application Ser. No. 15/788,733, filed Oct. 19, 2017, which is patented as U.S. Pat. No. 10,773,043, which claims the benefit of U.S. Provisional Patent Application No. 62/410,195 filed Oct. 19, 2016, the entire contents of which are incorporated by reference in their entireties.

FIELD OF THE INVENTION

The present invention relates generally to a medical device. More particularly, the present invention is related to a moisture removal and condensation and humidity management apparatus for a breathing circuit.

BACKGROUND

A breathing circuit delivers medical gas to a patient under pressure in a prescribed volume and breathing rate. The medical gas is often humidified by a humidifier located at or near the ventilator or respirator. The optimum respiratory circuit delivers 100% RH medical gases to the patient while reducing the amount of humidity and subsequent condensate delivered back to the ventilator through the expiratory limb. Therefore, the humidified gas has to travel through all or most of the tubing and has time to cool. Cooling of the gas leads to rainout or condensation in the breathing tube and collection of water within the breathing circuit.

Several possible solutions to the problem of rainout have been developed. One such proposed solution is a heating wire provided along the length of the tube. The wire may be provided within the interior of the tubing or alternatively may be embedded along the interior of the tubing. The wire heats the humidified gas traveling through the tubing to prevent the gas from cooling, thus preventing the problem of water condensing out of the gas traveling through the breathing circuit. However, the manufacture of such heated wire respiratory circuits can be time consuming and costly.

Another possible solution, which eliminates the heated wire, is to provide a water collection device somewhere within the breathing circuit. A water collection apparatus is typically placed in the expiratory limb of the respiratory circuit to collect and allow for manual removal of excessive condensation prior to the gases entering the ventilator or respirator. It is known that excessive condensate entering a ventilator or respirator from the expiratory limb of a respiratory circuit can harm the device.

Most frequently, the water collection device is designed to trap the condensed water vapor in a removable container. When the container is removed, a valve can be actuated to create a gas tight seal for the breathing circuit. However, this type of water collection device has to be monitored and manually emptied, causing risk of patient or caregiver infection. The removal of moisture and condensation management is not automatic. Furthermore, the removable container is often only at one discrete point along the breathing circuit and may need to be lowered to gravitationally collect liquid, which may be impractical.

Another possible solution is to provide a permeable membrane in the breathing circuit tubing which is permeable to water vapor but impermeable to liquid water, such that moisture inside the breathing gas flow inside such tubing dissipates to outside the tubing via such a membrane, and out to the ambient air surrounding the tubing. The problem with this solution is at least two-fold: first, such a thin walled membrane which is exposed to the surroundings can be easily punctured or damaged; and second, due to a relatively high humidity in the ambient conditions, there can be a limited humidity differential between the breathing gas flow and the ambient surroundings, so that the capacity for moisture to dissipate passively through the permeable membrane to ambient surroundings can also be limited.

Accordingly, it is desirable to provide an improved apparatus for removing or decreasing water vapor, moisture, and/or condensate in a breathing circuit. It is further desirable that the improved apparatus for removing water vapor, moisture or condensate from the breathing tube, eliminates the need to monitor the device or to heat the exhalation limb of the breathing tube, and is not dependent on the positioning of the device, protects the device and its moisture and humidity transmission mechanism from damage, and increases its capacity for moisture removal and condensation management in a breathing circuit.

SUMMARY OF THE INVENTION

The foregoing needs are met, to a great extent, by the present invention, wherein a moisture removal apparatus for a breathing circuit arranged between a patient and a ventilator is provided. The apparatus may include a breathing gas conduit configured to receive a flow of breathing gas having a first humidity level. The apparatus may include a dry gas conduit adjacent to at least a portion of the breathing gas conduit, the dry gas conduit being configured to receive a flow of dry gas having a second humidity level lower than the first humidity level. The apparatus may also include a feeding conduit extending through at least a portion of the dry gas conduit, the feeding conduit configured to introduce the dry gas into the dry gas conduit. The apparatus may further include a moisture transmission pathway configured to enable transfer of moisture from the breathing gas to the dry gas based on the humidity differential.

In some embodiments of the present invention, the breathing gas conduit may be configured for the breathing gas to flow from an upstream end of the apparatus to a downstream end of the apparatus, and the feeding conduit may include an inlet at the downstream end of the apparatus.

In some embodiments of the present invention, a flow control element may be connected to the inlet of the feeding conduit and configured to control the flow of the dry gas into the feeding conduit.

In some embodiments of the present invention, the feeding conduit includes an outlet at the downstream end of the apparatus.

In some embodiments of the present invention, the dry gas conduit may include a closed end at the upstream end of the apparatus.

In some embodiments of the present invention, the dry gas conduit may include an outlet at the downstream end of the apparatus.

In some embodiments of the present invention, the apparatus may include a filter connected to the outlet of the dry gas conduit.

In some embodiments of the present invention, the outlet of the dry gas conduit may be in communication with an ambient environment surrounding the apparatus.

In some embodiments of the present invention, the apparatus may include a source of suction connected to the outlet of the dry gas conduit.

In some embodiments of the present invention, the feeding conduit may extend through greater than half of the length of the dry gas conduit.

In some embodiments of the present invention, the moisture transmission pathway may include a permeable membrane which is permeable to water vapor but impermeable to liquid water.

In some embodiments of the present invention, the apparatus may include a second moisture transmission pathway including one or more perforations which permit drainage of liquid water from the breathing gas conduit to the dry gas conduit.

In some embodiments of the present invention, the moisture transmission pathway may include a first layer in contact with the breathing gas, the first layer having a first permeability; and a second layer in contact with the first layer, the second layer having a second permeability less than the first permeability In some embodiments of the present invention, the apparatus may include an inner tube defining the breathing gas conduit and including the moisture transmission pathway; and an outer tube surrounding the inner tube, the dry gas conduit being defined by an annular conduit between the inner tube and the outer tube.

In some embodiments of the present invention, the apparatus may include a tube defining the breathing gas conduit and the dry gas conduit, the tube may have a common dividing wall extending between the breathing gas conduit and the dry gas conduit, the common dividing wall including the moisture transmission pathway.

In some embodiments of the present invention, the moisture removal apparatus may be an expiratory limb of a ventilator circuit.

In another aspect of the present invention, a method of removing moisture from a breathing circuit is provided. The method may include receiving a flow of breathing gas having a first humidity level through a breathing gas conduit. The method may include supplying a flow of the dry gas into a dry gas conduit with a feeding conduit, the feeding conduit extending through at least a portion of the dry gas conduit. The method may also include receiving the flow of the dry gas into the dry gas conduit, the dry gas conduit being adjacent to at least a portion of the breathing gas conduit. The method may further include transferring moisture from the breathing gas to the dry with a moisture transmission pathway based on the humidity differential.

In some embodiments of the present invention, the breathing gas may flow through the breathing gas conduit from an upstream end to a downstream end, and the method may include introducing the dry gas into an inlet of the feeding conduit positioned at the downstream end of the breathing gas conduit.

In some embodiments of the present invention, the supplying the flow of the dry gas may be through an outlet of the feeding conduit positioned at the upstream end of the breathing gas conduit.

In some embodiments of the present invention, the transferring moisture may be performed with a permeable membrane which is permeable to water vapor but impermeable to liquid water.

In some embodiments of the present invention, the method may include expiring the breathing gas from a ventilator circuit into the breathing gas conduit.

There has thus been outlined, rather broadly, certain embodiments of the invention in order that the detailed description thereof herein may be better understood, and in order that the present contribution to the art may be better appreciated. There are additional embodiments of the invention that will be described below and which form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this invention is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
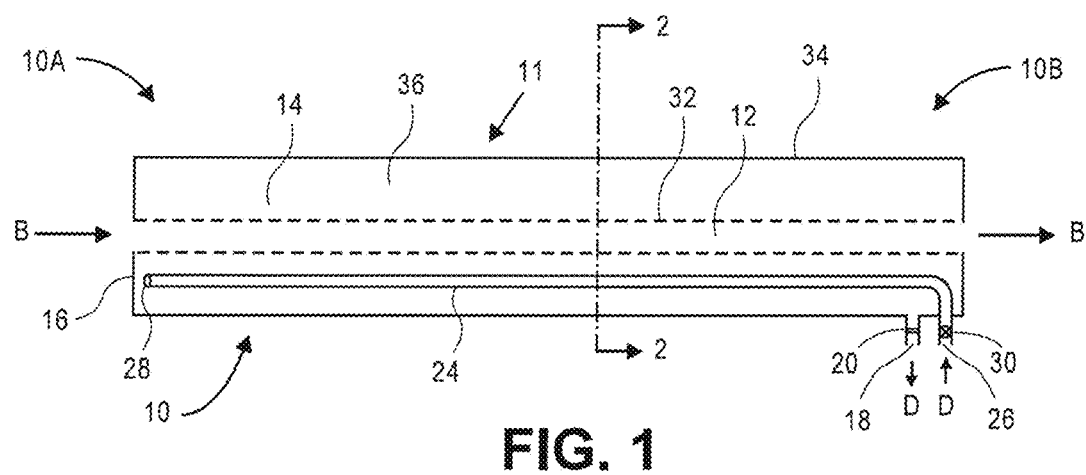
FIG. 1 is a schematic view illustrating an apparatus that may be incorporated into or as part of a breathing gas circuit in accordance with one or more embodiments of the present invention.

The invention will now be described with reference to the drawing figures, in which like parts are referred to with like reference numerals throughout. One or more embodiments in accordance with the present invention provide a moisture removal and condensation and humidity management apparatus for a breathing circuit to rapidly remove water vapor or condensate from a humidified medical gas traveling through a breathing circuit between a ventilator and a patient or the patient and the ventilator. As used herein, a "breathing circuit" or "breathing gas circuit" is any arrangement of tubes or conduits which carries gases to be administered to and from a patient, such as from a ventilator, and which may include additional accessories or devices attached to it. Such "breathing gases" may include oxygen, air or any component thereof, and are configured to absorb high levels of moisture and/or being humidified prior to administration to a patient, or during administration to a patient, suitable for medical applications.

FIG. 1 is a schematic view illustrating an apparatus 10 that may be incorporated into or as part of a breathing gas circuit in accordance with one or more embodiments of the present invention. The moisture removal and condensation and humidity management apparatus 10 for a breathing circuit may include a section or length of breathing circuit tubing 11 defining a breathing gas conduit 12 for a flow (B) of breathing gas therein. The breathing gas flows from a first, upstream end 10A of the apparatus 10 proximate to a patient, through the breathing gas conduit 12 defined within the apparatus 10, and to a second, downstream end 10B of the apparatus 10 distal of the patient. The breathing gas may have a first humidity level and a level of moisture therein, which may be calibrated by the user based on the needs of the patient. In some embodiments, the length of breathing circuit tubing 11 is in an expiratory limb of a breathing circuit, for example, positioned somewhere between a patient and a ventilator.

The apparatus 10 may also include a dry gas conduit 14 adjacent to at least a portion of the breathing gas conduit 12 between the upstream end 10A and downstream end 10B, for a dry gas flow (D) therein. The dry gas flow (D) is configured to have a second humidity level which is lower than the first humidity level within the breathing gas conduit (B). In some embodiments, the dry gas conduit 14 may extend the entire length of the breathing gas conduit 12 to optimize moisture transfer. However, in some embodiments, the dry gas conduit 14 may extend less than the entire length of the breathing gas conduit 12. The dry gas conduit 14 may include a closed end 16 on the upstream end 10A, and downstream end 10B and an outlet 18 at the downstream end 10B. The outlet 18 may be in communication with a source of suction and/or the ambient environment around the apparatus 10. In some embodiments, the outlet 18 may be in communication with a filter 20.

The apparatus 10 may further include a feeding conduit 24 configured to supply dry gas to the dry gas conduit 14. As depicted in FIG. 1, the feeding conduit 24 may include an inlet 26 at the downstream end 10B of the apparatus 10, and an outlet 28 at the first end 10B of the apparatus 10, such that the feeding conduit 24 extends through at least a portion of the dry gas conduit 14. For example, the feeding conduit 24 may extend greater than half of the length of the dry gas conduit 14. In some embodiments, the feeding conduit 24 may extend substantially the entire length of the dry gas conduit 14. Advantageously, the feeding conduit 24 may allow the inlet 26 and outlet 18 for dry gas of the apparatus 10 to be further away from the patient, reducing any potential safety risk to the patient. This prevents any potential sparking caused by the ingress and egress of the dry gas proximate the patient. Furthermore, by providing the outlet 18 of the feeding conduit 24 at the upstream end 10A within the dry gas conduit 14, the apparatus 10 may provide a large surface area for moisture/humidity transfer from the breathing gas conduit 12 to the dry gas conduit 14. In some embodiments, a flow or volume control element 30 (e.g., a valve) may be connected to the inlet 26 of the feeding conduit 24 and configured to control the flow of dry gas into the feeding conduit 24.

Figure 2:
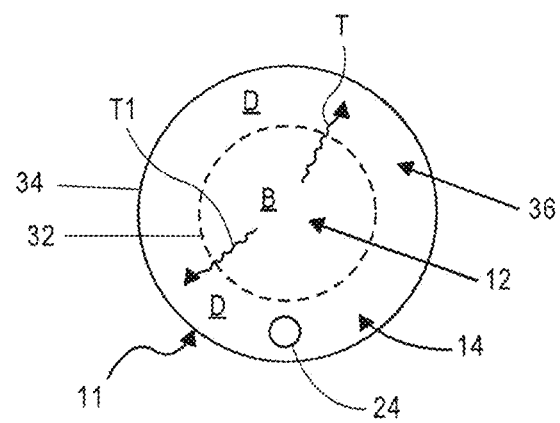
FIG. 2 is a schematic cross-sectional view illustrating the apparatus of FIG. 1 of one or more embodiments of the present invention.

FIG. 2 is a schematic cross-sectional view illustrating the apparatus 10 of FIG. 1 of one or more embodiments of the present invention. As shown in the embodiment of FIGS. 1-2, the dry gas conduit 14 may be an annular flow space which is concentric with breathing gas conduit 12. For example, the breathing circuit tubing 11 may include an inner tube 32 defining the breathing gas conduit 12, and an outer sleeve or tube 34 surrounding the inner tube 32 and defining the dry gas conduit 14. The dry gas conduit 14 thereby may include an annular conduit 36 defined between the inner tube 32 and outer tube 34. Alternatively, in some embodiments, the inner tube 32 may define the dry gas conduit 14 and the annular conduit 36 between the inner tube 32 and the outer tube 34 may include the breathing gas conduit 12. As depicted, the feeding conduit 24 may extend through the dry gas conduit 14. One or both, of the inner tube 32 and the outer tube 34 may include corrugated tubing. In the present invention, a moisture transmission pathway may be positioned between the breathing gas conduit 12 and the dry gas conduit 14. For example, a sufficient stretch of surface area of the breathing circuit tubing 11 may be shared between the breathing gas conduit 12 and the dry gas conduit 14 enabling transfer of moisture between the flow of breathing gas (B) and the flow of dry gas (D), as further described below.

The present invention provides one or more embodiments which provide the moisture transmission pathway between the breathing gas conduit 12 and the dry gas conduit 14, lowering the moisture and/or humidity in the flow of breathing gas (B) by transferring the moisture and/or humidity to the dry gas flow (D). For example, in FIG. 2, the moisture transmission pathway (T) may occur between the higher humidity breathing gases in breathing gas conduit 12 and the lower humidity dry gas flow in dry gas conduit 14. A user may increase or decrease the level of dry gas supplied to the dry gas conduit 14 to manage or remove the condensate which may be transferred from the breathing gas (B) to the dry gas (D). The moisture level thus may be reduced from within the breathing gas flow (B) and transferred to the dry gas flow (D).

In some embodiments, such as shown in FIG. 2, the breathing circuit tubing 11 may include a permeable portion or membrane (as depicted in broken lines) along part or all of the inner tube 32. The permeable portion may be permeable to water vapor but impermeable to liquid water, such that the moisture transmission pathway (T) is provided by the permeable portion of the breathing circuit tubing 11. The permeable portion may include one or more materials that are water vapor breathable and allow passage of water vapor, as is well known to those of ordinary skill in the art. The permeable portion may form some or all of the walls of the breathing gas conduit 12 (e.g., inner tube 32) and may include a single, or composite layer of water vapor breathable medium. For example, in some embodiments, the permeable portion may include an inner layer and an outer layer having different permeability/wicking properties. A first wicking layer may be provided as an inner layer of inner tube 32 and may be configured to contact the breathing gas flow (B) inside of the inner tube 32. The wicking layer may be made of one or more wicking materials that allow for adsorption and/or absorption of moisture and/or water in any phase (e.g., gas and/or liquid), for example, through capillary action. The permeable portion may also include an outer layer of water vapor breathable material that permits the passage of water vapor only, while not permitting passage of liquid water.

Examples of wicking material of the permeable portion include knitted and/or non-woven cloth or fabric. The wicking material may be natural and/or synthetic, such as polyester, polyester and polypropylene blends, nylon, polyethylene or paper. The wicking material may also include microfilaments and/or microfiber material such as Evolon® brand fabric material made by Freudenberg & Co. KG. One particular example of wicking material may be a non-woven material of 70% polypropylene and 30% polyester. Another example of the wicking material may be Evolon® brand fabric material having a weight of 60 or 80 grams per square meter. Examples of the outer layer of water vapor breathable material include Sympatex® brand water vapor permeable membranes made of polymers made by Sympatex Technologies, including monolithic hydrophilic polyester ester membrane, including, as one example, a 12 micron thick membrane. The outer tube 34 may include a more rigid material than the inner tube 32, to prevent the inner tube 32 from being damaged and/or punctured.

In some embodiments, the breathing circuit tubing 11 may, additionally or alternatively, include one or more small openings or perforations (not shown) in the inner tube 32 which permit drainage of liquid water from the breathing gas conduit 12 to the dry gas conduit 14. Therefore, a second moisture transmission pathway T1 may be provided by the one or more perforations between the breathing gas flow (B) and dry gas flow (D), as shown in FIG. 2. Although, the transmission pathway (T) and the second transmission pathway (T1) are depicted in the same cross-sectional view of FIG. 2, the transmission pathways (T, T1) may be provided in the alternative and/or at different portions along the breathing circuit tubing 11. The transmission pathway (T) and the second transmission pathway (T1) may be provided in a gradient along the length of the inner tube 32. For example, in some embodiments, the inner tube 32 may have more permeability at the upstream end 10A than the downstream end 10B, increasing moisture transfer when the breathing gas enters the breathing gas conduit 12 reducing condensation in remaining length of the inner tube 32. In some embodiments, the inner tube 32 may have more permeability on the downstream end 10B than the upstream end 10A, increasing moisture transfer when the moisture of the breathing gas is lower.

Figure 3:
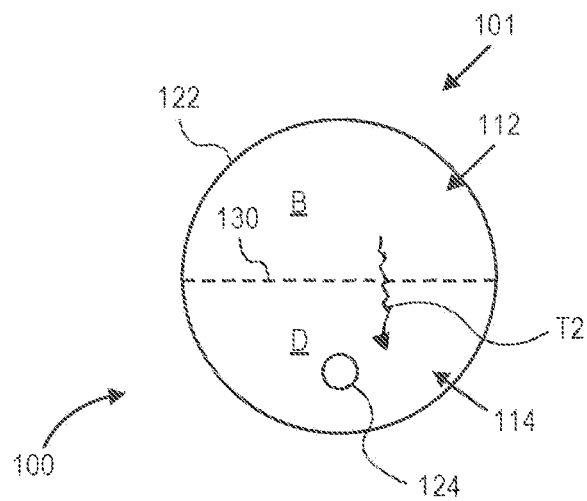
FIG. 3 is a schematic cross-sectional view illustrating the apparatus of FIG. 1 of one or more additional embodiments of the present invention.
Figure 4:
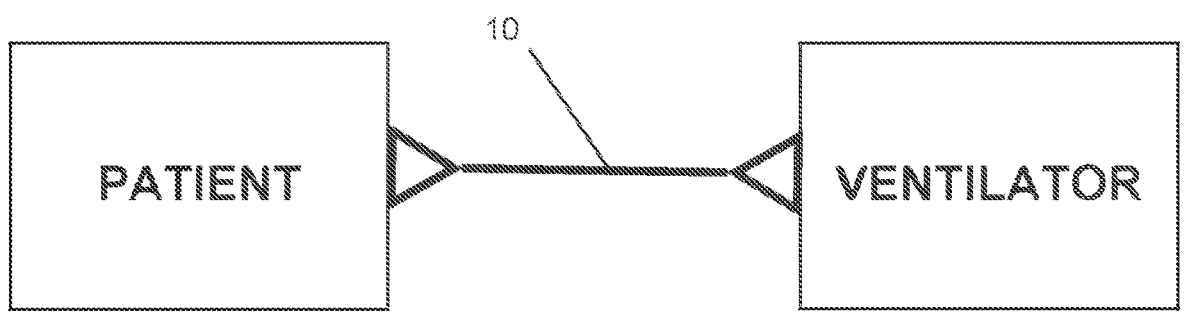
FIG. 4 is a schematic view of the apparatus positioned between a patient and a ventilator.

FIG. 3 is a schematic cross-sectional view illustrating the apparatus of FIG. 1 of one or more additional embodiments of the present invention. As depicted in FIG. 3, a breathing circuit tubing 101 may include a tube 122 including a breathing gas conduit 112 configured to receive a flow of breathing gas flow (B). The breathing gas may have a first humidity level and a first level of moisture. The tube 122 may also include a dry gas conduit 114 configured to receive a dry gas flow (D). The dry gas flow may have a second humidity level lower than the first humidity level, and/or a second level of moisture lower than the first level of moisture. The dry gas conduit 114 may be adjacent to at least a portion of the breathing gas conduit 112. A feeding conduit 124 may extend through the dry gas conduit 114. As further depicted in FIG. 3, a moisture transmission pathway (T2) may be provided between the breathing gas conduit 112 and the dry gas conduit 114, such that moisture and/or humidity may be transferred from the breathing gas (B) to the dry gas flow (D) based on the differential humidity/moisture levels. In the embodiment of FIG. 3, the breathing gas conduit 112 and dry gas conduit 114 may share a common dividing wall 130 providing the moisture transmission pathway (T2). For example, the moisture transmission pathway (T2) may be provided by a permeable portion or membrane (depicted as broken lines) incorporated into part or all of the dividing wall 130, as described herein, or a series of perforations in part or all of the dividing wall 130, as also described herein. The permeable portion may be permeable to water vapor but impermeable to liquid water and may include one or more layers, including a wicking layer, as described above.

In one or more embodiments of the present invention, the dry gas conduit 14, 114 may be closed to ambient air around the apparatus 10. The dry gas conduit 14, 114 therefore can be configured to provide a stream of dry gas flow at humidity levels which are significantly lower than the humidity in the breathing gas conduit 12, 112. In some embodiments, the apparatus 10 may include one or more sensors configured to detect the first humidity level of the breathing gas conduit 12 and the second humidity level of the dry gas conduit 14.

The present invention therefore uses the differential between humidity or moisture content between the respective flows in the breathing gas conduit 12, 112, compared to the dry gas conduit 14, 114, which allows for greater extraction or diffusion of moisture and humidity from the breathing gas flow to the dry gas flow, which is further assisted by the convective action of the dry gas flow along the common surface area shared between the breathing gas conduit 12, 112, and the dry gas conduit 14, 114, such as along inner tube 32, or common dividing wall 130.

The present invention therefore provides a superior way of removing moisture or water vapor from a breathing circuit, which is better than water traps or other fluid dissipation or moisture removal devices known in the prior art. The result of the inventive apparatus disclosed is that when the apparatus is coupled with a breathing circuit, rainout or condensation in the breathing tube and collection of water within the breathing circuit is significantly reduced. The present invention therefore allows for removal of the collected condensate on the inner walls of a breathing gas conduit, which may then be transported away through an outer sleeve or tube which provides the dry gas conduit. The outer tube of the apparatus can also protect the inner tube from damage or puncture, which can be especially vulnerable to damage or puncture when it incorporates a permeable membrane and/or perforations as described herein. To provide additional strength and puncture protection, an additional outer cover structure can be added to the apparatus. The present invention therefore represents an improvement over the known prior art by providing the benefits of: (a) reducing or eliminating user management of condensate levels within a breathing circuit, and/or (b) reducing the humidity output from an expiratory limb of a breathing circuit to reduce the collection of condensate which may be collected in the ventilator.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A moisture removal apparatus comprising:
    a breathing gas conduit that directs a flow of breathing gas in a first direction; and
    a dry gas conduit that directs a dry gas flow; and
    a moisture transmission pathway between the breathing gas conduit and the dry gas conduit that lowers a humidity of the breathing gas by transferring the humidity to the dry gas flow; and
    a feeding conduit configured to supply dry gas to the dry gas conduit in a second direction opposite the first direction.

2. The moisture removal apparatus of claim 1, wherein the feeding conduit extends greater than half a length of the dry gas conduit.

3. The moisture removal apparatus of claim 1, wherein the feeding conduit extends through the dry gas conduit.

4. The moisture removal apparatus of claim 1, wherein the feeding conduit includes an inlet and an outlet;
wherein upstream is defined relative to the flow of the breathing gas within the breathing gas conduit;
wherein the outlet is positioned upstream of the inlet; and
wherein the apparatus is an expiratory limb.

5. The moisture removal apparatus of claim 4, wherein the inlet of the feeding conduit is positioned at a first end of the apparatus; and
wherein the outlet of the feeding conduit is positioned at a second end of the apparatus opposite the first end of the apparatus.

6. The moisture removal apparatus of claim 5, wherein the first end of the apparatus is a downstream end of the apparatus;
wherein the second end of the apparatus is an upstream end of the apparatus; and
wherein the flow of the breathing gas flows from the upstream end of the apparatus to the downstream end of the apparatus within the breathing gas conduit.

7. The moisture removal apparatus of claim 1, further comprising:
an inner tube that defines the breathing gas conduit; and
an outer tube surrounding the inner tube, the dry gas conduit being defined by an annular space between the inner tube and the outer tube.

8. The moisture removal apparatus of claim 1, further comprising a breathing circuit tube that includes the breathing gas conduit, the dry gas conduit, the moisture transmission pathway, and the feeding conduit.

9. The moisture removal apparatus of claim 1, wherein the feeding conduit includes an inlet and further comprising an outlet fluidly coupled to the dry gas conduit.

10. The moisture removal apparatus of claim 9, further comprising a filter fluidly coupled to the outlet.

11. The moisture removal apparatus of claim 1, wherein a width of the feeding conduit is smaller than a width of the dry gas conduit.

12. A moisture removal apparatus comprising:
a breathing gas conduit that directs a flow of breathing gas; and
a dry gas conduit that directs a dry gas flow; and
a moisture transmission pathway between the breathing gas conduit and the dry gas conduit that lowers a humidity of the breathing gas by transferring the humidity to the dry gas flow;
a feeding conduit having an inlet and an outlet, the outlet of the feeding conduit being positioned upstream of the inlet of the feeding conduit; and
wherein upstream is defined relative to the flow of the breathing gas within the breathing gas conduit.

13. The moisture removal apparatus of claim 12, wherein the inlet of the feeding conduit is positioned at a first end of the apparatus; and
wherein the outlet of the feeding conduit is positioned at a second end of the apparatus opposite the first end of the apparatus.

14. The moisture removal apparatus of claim 13, wherein the first end of the apparatus is a downstream end of the apparatus;
wherein the second end of the apparatus is an upstream end of the apparatus; and
wherein the flow of the breathing gas flows from the upstream end of the apparatus to the downstream end of the apparatus within the breathing gas conduit.

15. The moisture removal apparatus of claim 12, wherein the outlet is a first outlet and further comprising a second outlet fluidly coupled to the dry gas conduit; and
wherein the second outlet is fluidly coupled to the ambient environment.

16. The moisture removal apparatus of claim 12, further comprising:
an inner tube that defines the breathing gas conduit; and
an outer tube surrounding the inner tube, the dry gas conduit being defined by an annular space between the inner tube and the outer tube.

17. A moisture removal apparatus comprising:
a breathing gas conduit that directs a flow of breathing gas; and
a dry gas conduit that directs a dry gas flow; and
a moisture transmission pathway between the breathing gas conduit and the dry gas conduit that lowers a humidity of the breathing gas by transferring the humidity to the dry gas flow;
a feeding conduit configured to supply dry gas to the dry gas conduit, the feeding conduit having a first inlet and a first outlet; and
a second outlet fluidly coupled to the dry gas conduit; and
wherein the second outlet and the first inlet are positioned at a first end of the apparatus opposite a second end of the apparatus;
wherein the first outlet of the feeding conduit is positioned upstream of the first inlet of the feeding conduit;
wherein upstream is defined relative to the flow of breathing gas within the breathing gas conduit.

18. The moisture removal apparatus of claim 17, wherein the first end of the apparatus is a downstream end of the apparatus;
wherein the second end is an upstream end of the apparatus; and
wherein the flow of the breathing gas flows from the upstream end of the apparatus to the downstream end of the apparatus within the breathing gas conduit.

19. The moisture removal apparatus of claim 17, further comprising:
an inner tube that defines the breathing gas conduit; and
an outer tube surrounding the inner tube, the dry gas conduit being defined by an annular space between the inner tube and the outer tube.

20. The moisture removal apparatus of claim 17, wherein the feeding conduit at least partially extends within the dry gas conduit.

* * * * *